(12) United States Patent
Antonelli et al.

(10) Patent No.: US 7,010,987 B2
(45) Date of Patent: Mar. 14, 2006

(54) NON-DESTRUCTIVE METHOD OF DETECTING DEFECTS IN BRAZE-REPAIRED CRACKS

(75) Inventors: Giampiero Antonelli, Monza (IT); Andreas Boegli, Vogelsang (CH); Klaus Germerdonk, Ennetbaden (CH); Alexander Schnell, Ennetbaden (CH)

(73) Assignee: ALSTOM (Switzerland) Ltd, Baden (CH)

( * ) Notice: Subject to any disclaimer, the term of this patent is extended or adjusted under 35 U.S.C. 154(b) by 0 days.

(21) Appl. No.: 10/697,150

(22) Filed: Oct. 31, 2003

(65) Prior Publication Data

US 2004/0139805 A1   Jul. 22, 2004

(30) Foreign Application Priority Data

Oct. 31, 2002   (EP) .................................. 02405932

(51) Int. Cl.
*G01N 19/08* (2006.01)
(52) U.S. Cl. .............................. 73/799; 73/788; 73/803
(58) Field of Classification Search ............... 73/788, 73/799, 760, 803
See application file for complete search history.

(56) References Cited

U.S. PATENT DOCUMENTS

| | | | |
|---|---|---|---|
| 4,188,237 A | | 2/1980 | Chasteen |
| 4,285,459 A | * | 8/1981 | Baladjanian et al. .... 29/402.07 |
| 4,643,782 A | | 2/1987 | Harris et al. |
| 4,739,261 A | * | 4/1988 | Sugiyama et al. .......... 324/232 |
| 5,071,054 A | * | 12/1991 | Dzugan et al. ............. 29/889.1 |
| 5,071,486 A | | 12/1991 | Chasteen |
| 5,237,271 A | * | 8/1993 | Hedengren ................... 324/232 |
| 5,666,643 A | | 9/1997 | Chesnes et al. |
| 5,728,227 A | | 3/1998 | Reverman |
| 5,732,467 A | | 3/1998 | White et al. |
| 5,759,301 A | | 6/1998 | Konter et al. |
| 5,888,451 A | | 3/1999 | Konter et al. |
| 6,193,145 B1 | * | 2/2001 | Fournier et al. ........ 228/262.41 |
| 6,530,971 B1 | * | 3/2003 | Cohen et al. .................. 75/254 |
| 6,701,615 B1 | * | 3/2004 | Harding et al. ........... 29/402.07 |

FOREIGN PATENT DOCUMENTS

| | | |
|---|---|---|
| DE | 885489 | 8/1953 |
| EP | 0034041 | 3/1985 |
| WO | 01/22076 | 3/2001 |

OTHER PUBLICATIONS

Rao et al, "An artificial neural network for eddy current testing of austenitic stainless steel welds", *NDT& E International*, vol. 35, No. 6, pp. 393-398 (2002), Elsevier Science Ltd, Butterworth-Heinemann, Oxford, Great Britian, XP 004365970.

Burke, "Crack depth measurement using Eddy-Current NDE", pp. 1-10, presented at *Destructive Testing*, Sep. 17-21, 2001, Brisbane, Australia.

(Continued)

*Primary Examiner*—Max Noori
*Assistant Examiner*—Alandra Ellington
(74) *Attorney, Agent, or Firm*—Buchanan Ingersoll PC

(57) ABSTRACT

It is disclosed a method of detecting and quantifying subsurface defects (10) in an article (1) made of high strength non magnetisable materials after the use in a high temperature environment. A crack (8) or gap on a surface (7) of the article (1) is brazed and after the brazing operation the crack (8) or any remaining braze defect or subsurface crack (10) is detected and quantified by means of a multifrequency eddy current system.

20 Claims, 3 Drawing Sheets

OTHER PUBLICATIONS

Figure 1:
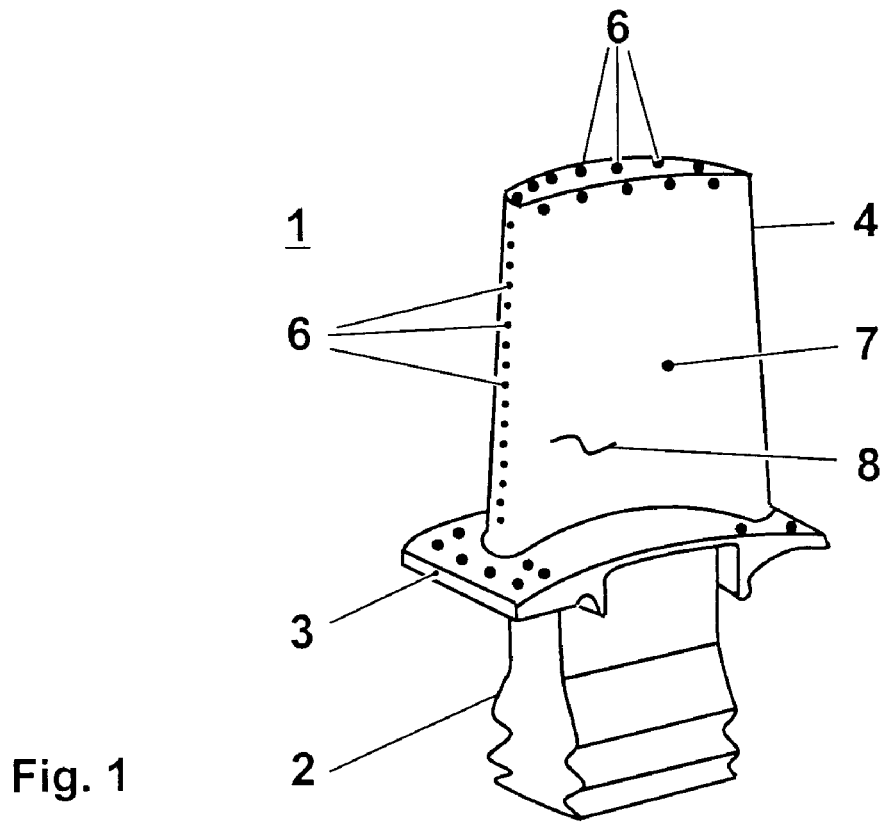

Antonelli et al, "Qualification of a Frequency Scanning Eddy Current Equipment For Nondestructive Characterization of New and Serviced High-Temperature Coatings", *Proceedings of ASME Turbo Expo 2001*, Jun. 4-7, 2001, New Orleans, Louisiana, ASME paper No. 2001-GT-0419.

Antonelli et al, Non-Destructive Condition Assessment of Serviced MCrAlY Coatings, presented at *Turbine Forum on Advanced Coatings for High Temperatures*, Nice, France, pp. 1-12.

* cited by examiner

NON-DESTRUCTIVE METHOD OF DETECTING DEFECTS IN BRAZE-REPAIRED CRACKS

TECHNICAL FIELD

The invention relates to a non-destructive method of detecting and quantifying subsurface defects in an article after brazing.

STATE OF THE ART

The wide use of single crystal (SX) and directionally solidified (DS) components allows an increased turbine inlet temperature and therefore an increased turbine efficiency as well. Alloys, specially designed for SX/DS casting, were developed in order to make maximum use of material strength and temperature capability. During operation of such components under high temperature conditions, various types of damages can occur. For example, cracks can result from thermal cycling and foreign object impact. In addition, cracks and inclusions may be incurred during manufacture. Because the cost of the components formed from high temperature nickel base superalloys is relatively high, it is usually more desirable to repair these components than to replace them.

The following state of the art methods for repairing high temperature superalloys are generally known:

U.S. Pat. No. 5,732,467 discloses a method of repairing cracks on the outermost surface of an article having a directionally oriented microstructure and a superalloy composition. The repairing is done by coating the cleaned crack surface with a material featuring the same material composition as the article. Thereby the coated crack surface is subjected to an elevated temperature and isostatic pressure over a period of time sufficient to repair the crack surface without changing the crystalline microstructure of the parent article.

In addition, a number of alternative methods of brazing for repairing cracks or gaps are known. U.S. Pat. No. 5,666,643 discloses a braze material for repairing an article, in particular components made from a cobalt and a nickel-base superalloy, such as gas turbine engine parts. The braze material is composed of particles featuring a high melting temperature which are distributed within the a braze alloy. These particles could be of single crystal, directionally solidified, or equiaxed microstructure.

Existing NDE-techniques have limited capabilities to quantitatively characterize any remaining subsurface brazing defect in complex geometries like gas turbine blades and vanes. Especially, Eddy Current techniques of prior art can not be applied on geometries with locally changing wall thickness in the range of the penetration depth of the eddy current sensor. They are not able to give quantitative information on defect size and in-depth location in varying geometries as Burke, S. K, G., 2001, "Crack depth measurement using Eddy Current NDE", presented at Destructive Testing, Sep. 17–21, 2001, Brisbane, AUS discloses.

SUMMARY OF INVENTION

It is the aim of the present invention to find a non destructive testing method for the quality control of high temperature brazed cracks or gaps made of article made of high strength non magnetisable materials such as blades or vanes of gas turbines made from a nickel base superalloy.

This objective is solved by method of detecting and quantifying subsurface defects in an article made of high strength non magnetisable materials after the use in a high temperature environment, the article exhibiting a crack or gap on a surface, the method comprising the steps of
  (a) the crack or gap is brazed and
  (a) after the brazing operation any remaining braze defect or subsurface crack is detected and quantified by means of a multifrequency scanning eddy current system.

Thereby, it is possible to determine the distance of remaining braze defects or subsurface cracks after brazing from the accessible surface of the component and the depth of the remaining crack, gap or defect. Dependent on the measured extent of the remaining crack after brazing a decision can be made concerning the fulfillment of the serviceability of the quality requirements of the braze or concerning further usability of the article.

In addition, the surface of the crack or gap may be cleaned from oxides by using any means known in the state of the art such as Floride Ion Cleaning (FIC), other halide cleaning, hydrogen cleaning, salt bath cleaning, any combination thereof or other means, which is widely known in state of the art.

In one embodiment of the present invention, the method is applied to blades or vanes of gas turbines from a nickel base superalloy.

SHORT SUMMARY OF DRAWINGS

Figure 2:
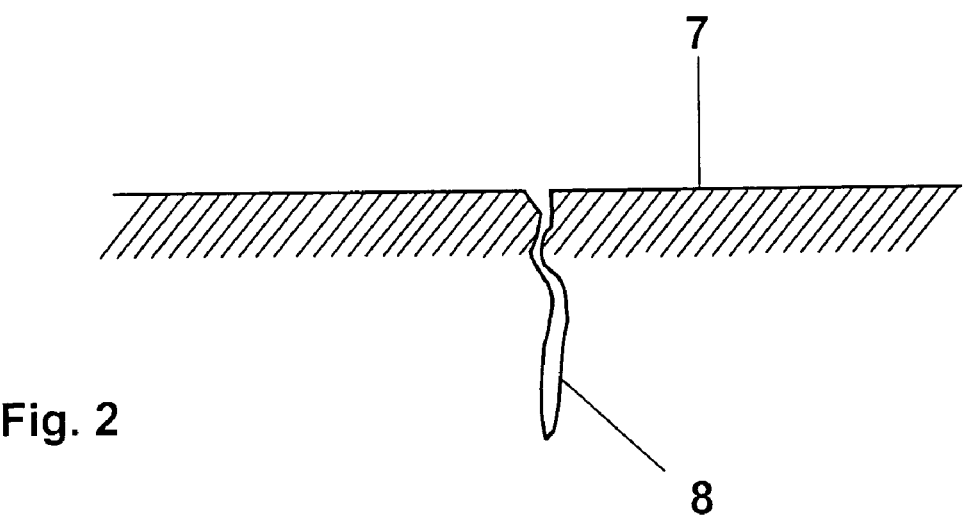
Figure 3:
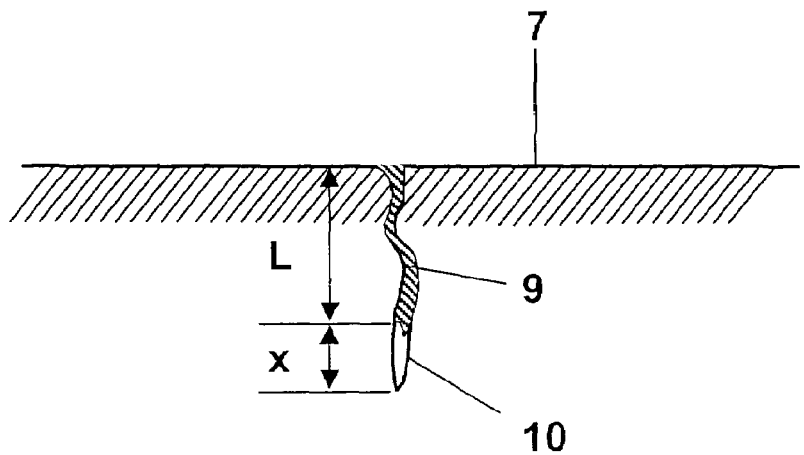
Figure 4:
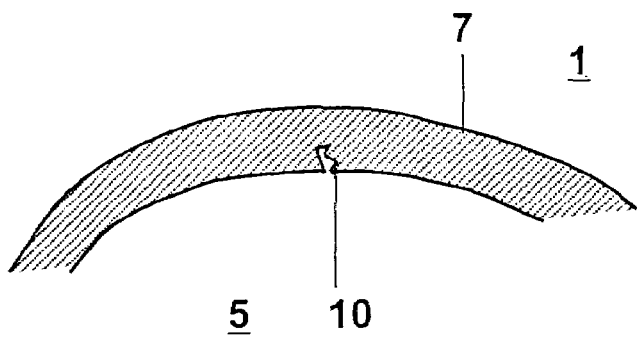
Figure 5:
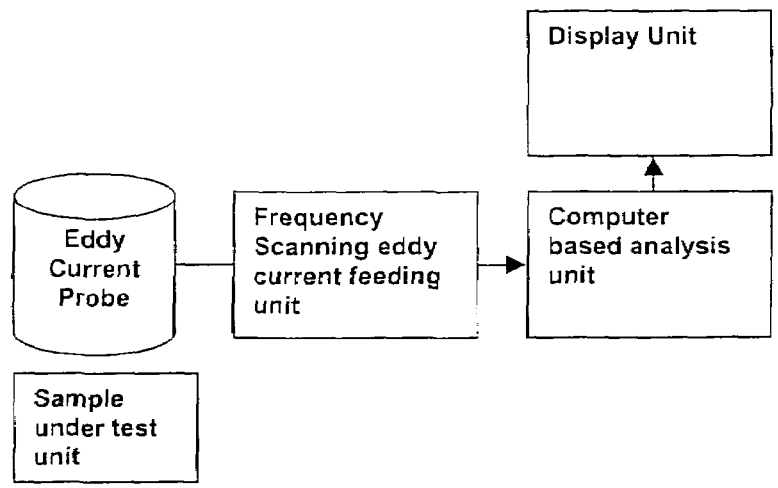
Figure 6:
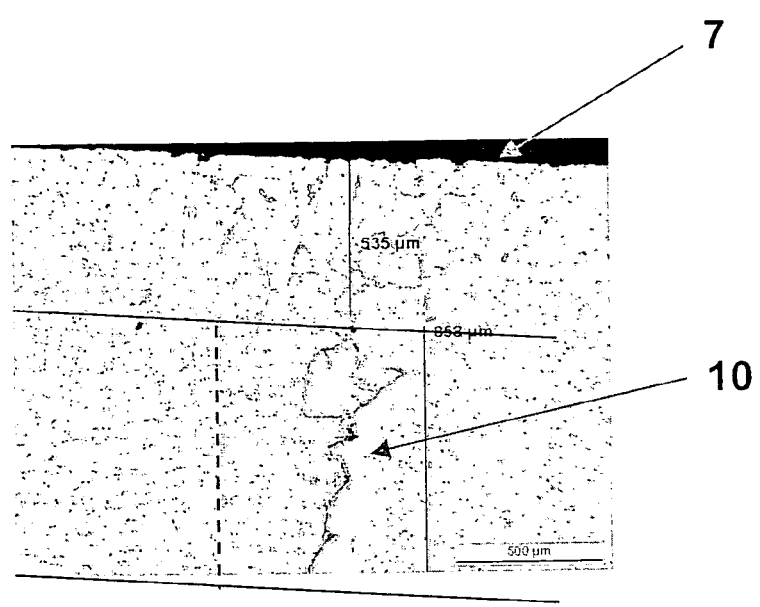

The invention is illustrated by the accompanying drawings, in which
  FIG. 1 shows a turbine blade,
  FIG. 2 shows a crack on the external surface of the blade,
  FIG. 3 shows a brazed repaired crack,
  FIG. 4 shows a crack on the internal surface of the blade
  FIG. 5 shows a schematic drawing of a multifrequency scanning eddy current system and
  FIG. 6 shows a not fully brazed crack in a component.

The enclosed drawings show only the parts important for the invention.

PREFERRED EMBODIMENT OF THE INVENTION

The invention relates to a method for the quality control of brazed cracks or gaps in a single crystal article 1 made of a Nickel base superalloy. Nickel base superalloys are known in the state of the art, e.g. from the document U.S. Pat. No. 5,888,451, U.S. Pat. No. 5,759,301 or from U.S. Pat. No. 4,643,782, which is known as "CMSX-4". As an example, FIG. 1 shows an article 1 such as blades or vanes of gas turbine engines, the gas turbine blade comprising a root portion 2, a platform 3 and a blade 4 with an internal cavity 5, not shown in FIG. 1, and cooling holes 6. The component 1 exhibits cracks 8 and gaps somewhere on an external surface 7 after being exposed to the hot gases of the gas turbine.

As shown in detail and in way of an example in FIG. 2, the external surface 7 of the component 1 exhibits a crack 8 which has to be repaired. As a preparation before applying the method of brazing, a protective coating such as MCrAlY or thermal barrier coating (TBC), has to be removed by a process of acid stripping, grit blasting or mechanical grinding. At the same time this method also cleans the surface layer of the parent material from unwanted oxides, debris, corrosion products or other contaminants. In addition, the surface of the crack or gap may be cleaned from oxides by using any means known in the state of the art such as Floride Ion Cleaning (FIC), other halide cleaning, hydrogen cleaning, salt bath cleaning, any combination thereof or other means, which is widely known in state of the art. The FIC process removes the stable $Al_2O_3$ oxides and depletes Al from the surface, thereby improving the braze flow and the repair of the cracked components. The process subjects the oxidized (and sulphidized) components to a highly reducing gaseous atmosphere of hydrogen and hydrogen fluoride at high temperatures, which may vary from 900° C. to 1000° C. Such FIC-processes are disclosed, for example, in EP-B1-34041, U.S. Pat. No. 4,188,237, U.S. Pat. No. 5,728,227 or in U.S. Pat. No. 5,071,486. After successful completion of the brazing method according the invention, the component will be recoated.

The crack 8 is subsequently repaired by any kind of brazing known from the state of the art and using an appropriate brazing filler material 9. The result is shown in FIG. 3. In a length L the crack 8 is repaired by the brazing operation in an adequate manner and the brazing material 9 filled the crack 8 properly, whereas other locations shows braze defects or subsurface cracks 10. The remaining subsurface crack 10 has a depth of x. It may be that any kind of other subsurface braze defect 10 occurs during the brazing operation. Thus, the remaining subsurface cracks or braze defects 10, which were not properly filled with braze material 9 during the repair operation, will be detected and quantified by any means of a multifrequency scanning eddy current system.

As an example such a multifrequency scanning eddy current system as described is described in Antonelli, G., Crisafulli, P., Tirone, G., 2001, "Qualification of a Frequency Scanning Eddy Current Equipment for Nondestructive Characterization of New and Serviced High-Temperature Coatings," ASME paper No. 2001-GT-0419 and Antonelli, G., 2002, "Non-Destructive Condition Assessment of MCrAlY Coatings", presented at Turbine Forum on Advanced Coatings for High Temperatures, Nice, France. This system was developed for non-destructive condition assessment of new and service exposed high-temperature coatings applied on the hot gas-path components of land-based gas turbines.

A schematic view of the system is given in FIG. 5. It is a portable system consisting of following modules:

Probe with combined or separated transmit-receiver coils,

Eddy current frequency scanning range from 10 kHz to 10 MHz,

Feeding and conditioning unit with high sensitivity and high stability,

Computer based data analysis unit and

Display unit

The system fully exploits the capabilities of multiple-frequency eddy current techniques in the characterisation of multiple-layer materials, based on the evaluation of even quite small differences in the electrical conductivity values of the different layers.

The idea of applying the eddy current system to the problem of subsurface crack characterisation relies on an assumption strengthened by initial tests, i.e. the possibility to approximate the local reduction in the effective conductivity due to crack presence, with a conductivity reduction in an horizontal layer of the test material. The estimation of the interface positions L1, L2 and conductivity values σ1, σ2, σ3 of each layer, given by the eddy current system, can be directly correlated with crack parameters such as: ligament thickness (crack distance from surface) L, crack depth x (see FIG. 3) There is no requirement of a calibration procedure on the specific samples to be tested.

In the present invention, after the brazing operation the brazed areas are inspected on a grid of points by an eddy current probe connected to a frequency scanning eddy current system. The signal obtained from the system at each inspected point is analysed by means of an algorithm which fits the signal with a calculated signal obtained from a simple model of the interaction between the probe and a multiple layer material, each layer of which is plane, homogeneous, and characterized by a value of electrical conductivity and positions of the interface with the adjacent layers. The effect on the signal due to presence of a subsurface defect 10 is approximated by a reduction of the electrical conductivity in a layer corresponding to the position of the subsurface defect 10 in the thickness of the material.

From said algorithm estimates are obtained of the conductivity values and the positions of the interfaces of each layers of the model. The presence of subsurface defects 10 is detected by comparing the estimated conductivity values obtained from the said algorithm with reference values obtained in the same way on a defect-free component. The ligament and the depth of the subsurface defects 10 are determined from the estimated positions of the interfaces between the model layers.

Local variations of the thickness of the component in the range of penetration of the eddy currents, the presence or fins or ribs on the inner surface of the component or the presence of an inner layer of air between two airfoils can be suppressed as an interfering quantity in the measurement by including in the model one or more layers describing the said geometric features of the component.

Dependent on the measured extent of the remaining crack after brazing a decision can be made concerning the fulfillment of the serviceability of the quality requirements of the braze or concerning further usability of the article.

Typical geometries of cracks for an application of the present invention are shown in FIG. 3 and FIG. 4.

FIG. 6 shows a not fully brazed crack 10 in a component. The graphical comparison between real crack geometry and estimation by the eddy current system of crack dimensions is shown. The layer where eddy current analysis placed the discontinuity is marked with a dotted line.

REFERENCE LIST

1 Article
2 Root portion
3 Platform
4 Blade
5 Cavity
6 Cooling holes
7 External surface of article 1
8 Crack
9 Brazing material
10 Braze defect or subsurface crack
x Crack depth
L Ligament thickness, crack distance from surface 7

What is claimed is:

1. A method of detecting and quantifying a subsurface crack in an article made of high strength non-magnetisable materials after using the article in a high temperature environment, the article exhibiting a crack on a surface, the method comprising the steps of:

(a) brazing the crack using a filler material having an electrical conductivity different from the electrical conductivity of the non-magnetisable materials; and (b) detecting and quantifying by means of a multi-frequency scanning eddy current system any subsurface cracks that remain beneath the brazed crack after the brazing.

2. The method according to claim 1, wherein the method is applied to blades or vanes of gas turbines made from a nickel base superalloy as the article.

3. The method according to claim 1, wherein the distance of the subsurface crack from a surface and the depth of the subsurface crack are determined.

4. The method according to claim 1, wherein dependent on the measured extent of the subsurface crack after brazing, a decision is made concerning the fulfillment of the serviceability of the quality requirements of the braze.

5. The method according to claim 1, wherein dependent on the extent of the remaining subsurface crack after brazing, estimated by the method, a decision is made concerning further usability of the article.

6. The method according to claim 1, wherein the surface of the crack is cleaned from oxides before applying the method.

7. The method according to claim 1, wherein a Flouride-Ion-Cleaning-Method is used for cleaning the surface before applying the process.

8. The method according to claim 1, wherein the surface is flat.

9. The method according to claim 1, wherein the surface is curved.

10. The method according to claim 1, wherein the surface is an external surface of the article.

11. The method according to claim 1, wherein the surface defines a cavity of the article.

12. A method of detecting and quantifying a subsurface crack in an article made of high strength non-magnetisable materials after using the article in a high temperature environment, the article exhibiting a crack on a surface, the method comprising:
(a) brazing the crack; and
(b) detecting and quantifying by means of a multi-frequency scanning eddy current system any subsurface cracks that remain beneath the brazed crack after the brazing;
wherein:
after the brazing operation, the brazed areas are inspected on a grid of points by an eddy current probe connected to a frequency scanning eddy current system;
the signal obtained from the system at each inspected point is analysed by means of an algorithm which fits the signal with a calculated signal obtained from a simple model of the interaction between the probe and a multiple layer material, each layer of which is plane, homogeneous, and characterized by a value of electrical conductivity and positions of the interface with the adjacent layers, wherein the effect on the signal due to presence of a subsurface crack is approximated by a reduction of the electrical conductivity in a layer corresponding to the position of the subsurface crack in the thickness of the material;
from the algorithm estimates are obtained of the conductivity values and the positions of the interfaces of each of the layers of the model;
the presence of the subsurface crack is detected by comparing the estimated conductivity values obtained from the algorithm with reference values obtained in the same way on a defect-free component;
the depth of the subsurface crack is determined from the estimated positions of the interfaces between the model layers.

13. A method of detecting and quantifying a subsurface crack in an article made of high strength non-magnetisable materials after using the article in a high temperature environment, the article exhibiting a crack on a surface, the method comprising:
(a) brazing the crack; and
(b) detecting and quantifying by means of a multi-frequency scanning eddy current system any subsurface cracks that remain beneath the brazed crack after the brazing;
wherein:
the distance of the subsurface crack from the surface and the depth of the subsurface crack are determined; and
(i) local variations of the thickness of the article in the range of penetration of the eddy currents, (ii) or the presence or fins or ribs on the inner surface of the article, or (iii) the presence of an inner layer of air between two airfoils, is suppressed as an interfering quantity in the measurement by including in the model one or more layers describing the geometric features of the article.

14. A method of detecting and quantifying a subsurface crack in a blade or vane of a gas turbine made of high strength non-magnetisable materials after using the blade or vane in a high temperature environment, the blade or vane having a crack on a surface, the method comprising:
brazing the crack using a filler material having an electrical conductivity different from the electrical conductivity of the non-magnetisable materials; and
detecting and quantifying using a multi-frequency scanning eddy current system any subsurface cracks that remain beneath the brazed crack after the brazing.

15. The method according to claim 14, wherein the surface of the crack is cleaned from oxides before applying the method.

16. The method according to claim 14, wherein the distance of the subsurface crack from a surface and the depth of the subsurface crack are determined.

17. The method according to claim 14, wherein the surface is flat.

18. The method according to claim 14, wherein the surface is curved.

19. The method according to claim 14, wherein the surface is an external surface of the blade or vane.

20. The method according to claim 14, wherein the surface defines a cavity of the blade or vane.

* * * * *